United States Patent
Calle et al.

(10) Patent No.: US 9,403,003 B2
(45) Date of Patent: Aug. 2, 2016

(54) METHODS AND SYSTEMS FOR FITTING A SOUND PROCESSOR TO A PATIENT USING A PLURALITY OF PRE-LOADED SOUND PROCESSING PROGRAMS

(75) Inventors: Guillermo A. Calle, Moorpark, CA (US); Kevin Hood, Coquitlam (CA)

(73) Assignee: Advanced Bionics AG, Staefa (CH)

( * ) Notice: Subject to any disclaimer, the term of this patent is extended or adjusted under 35 U.S.C. 154(b) by 1013 days.

(21) Appl. No.: 12/847,089

(22) Filed: Jul. 30, 2010

(65) Prior Publication Data

US 2012/0029593 A1 Feb. 2, 2012

(51) Int. Cl.
*A61N 1/00* (2006.01)
*A61N 1/36* (2006.01)
*A61N 1/372* (2006.01)
*H04R 25/00* (2006.01)
*A61N 1/05* (2006.01)

(52) U.S. Cl.
CPC ........ *A61N 1/36032* (2013.01); *A61N 1/37247* (2013.01); *A61N 1/37264* (2013.01); *H04R 25/70* (2013.01); *A61N 1/0541* (2013.01); *H04R 2225/41* (2013.01)

(58) Field of Classification Search
CPC ............. A61N 1/00; A61N 1/04; A61N 1/05; A61N 1/06; A61N 1/36032; A61N 1/0541
USPC ................ 607/52, 55–57, 136–137
See application file for complete search history.

(56) References Cited

U.S. PATENT DOCUMENTS

| | | | |
|---|---|---|---|
| 8,401,656 B2 * | 3/2013 | Smoorenburg | 607/57 |
| 8,612,011 B2 * | 12/2013 | Seligman | 607/55 |
| 2004/0047474 A1 | 3/2004 | Vries et al. | |
| 2004/0143304 A1 | 7/2004 | Hall et al. | |
| 2008/0267434 A1 | 10/2008 | Schumaier | |
| 2008/0307162 A1 | 12/2008 | Maeda et al. | |
| 2009/0024185 A1 * | 1/2009 | Kulkarni | A61N 1/36032 607/57 |
| 2010/0030130 A1 | 2/2010 | Parker et al. | |
| 2011/0106209 A1 * | 5/2011 | Saoji | 607/57 |

OTHER PUBLICATIONS

International Search Report and Written Opinion received in International Application No. PCT/US2011/045671, dated Oct. 21, 2011.

* cited by examiner

*Primary Examiner* — Christopher D Koharski
*Assistant Examiner* — Elizabeth K So
(74) *Attorney, Agent, or Firm* — ALG Intellectual Property, LLC

(57) ABSTRACT

An exemplary method of fitting a sound processor to a cochlear implant patient includes pre-loading program data representative of a plurality of sound processing programs onto a sound processor during a data transfer session and selectively using, after completion of the data transfer session, one or more of the pre-loaded sound processing programs to fit the sound processor to the patient. Corresponding methods and systems are also described.

9 Claims, 10 Drawing Sheets

METHODS AND SYSTEMS FOR FITTING A SOUND PROCESSOR TO A PATIENT USING A PLURALITY OF PRE-LOADED SOUND PROCESSING PROGRAMS

BACKGROUND INFORMATION

The natural sense of hearing in human beings involves the use of hair cells in the cochlea that convert or transduce acoustic signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be overcome through the use of conventional hearing aids that amplify sound so that acoustic signals can reach the hair cells within the cochlea. Some types of conductive hearing loss may also be treated by surgical procedures.

Sensorineural hearing loss, on the other hand, is caused by the absence or destruction of the hair cells in the cochlea which are needed to transduce acoustic signals into auditory nerve impulses. People who suffer from sensorineural hearing loss may be unable to derive significant benefit from conventional hearing aid systems, no matter how loud the acoustic stimulus. This is because the mechanism for transducing sound energy into auditory nerve impulses has been damaged. Thus, in the absence of properly functioning hair cells, auditory nerve impulses cannot be generated directly from sounds.

To overcome sensorineural hearing loss, numerous cochlear implant systems—or cochlear prostheses—have been developed. Cochlear implant systems bypass the hair cells in the cochlea by presenting electrical stimulation directly to the auditory nerve fibers by way of one or more channels formed by an array of electrodes implanted in the cochlea. Direct stimulation of the auditory nerve fibers leads to the perception of sound in the brain and at least partial restoration of hearing function.

When a cochlear implant system is initially implanted in a patient, and during follow-up tests and checkups thereafter, it is usually necessary to fit the cochlear implant system to the patient. Fitting of a cochlear implant system to a patient is typically performed by an audiologist or the like who presents various stimuli to the patient and relies on subjective feedback from the patient as to how such stimuli are perceived.

It is often desirable during a fitting session to direct a sound processor to operate in accordance with a variety of different sound processing programs. However, each time the sound processor is directed to switch from one sound processing program to another, the new sound processing program has to be loaded onto the sound processor. This process can take a relatively long amount of time (e.g., 20 seconds or more) during which the sound processor is inoperable. Such delays are frustrating to both the audiologist and the patient and often make it difficult to optimally fit the cochlear implant system to the patient.

SUMMARY

An exemplary method of fitting a sound processor to a cochlear implant patient includes pre-loading program data representative of a plurality of sound processing programs onto the sound processor during a data transfer session and selectively using, after completion of the data transfer session, one or more of the pre-loaded sound processing programs to fit the sound processor to the patient.

Another exemplary method of fitting a sound processor to a cochlear implant patient includes 1) pre-loading program data representative of a plurality of sound processing programs onto the sound processor during a data transfer session, 2) receiving, after completion of the data transfer session, user input representative of a selection of a first sound processing program included in the plurality of sound processing programs, 3) directing, in response to the user input, the sound processor to operate in accordance with the first sound processing program, 4) receiving, while the sound processor is operating in accordance with the first sound processing program, additional user input representative of a selection of a second sound processing program included in the plurality of sound processing programs, and 5) directing, in response to the additional user input, the sound processor to dynamically cease operating in accordance with the first sound processing program and begin operating in accordance with the second sound processing program.

An exemplary system for fitting a sound processor to a cochlear implant patient includes a data program loading facility configured to pre-load program data representative of a plurality of sound processing programs onto the sound processor during a data transfer session and a fitting facility selectively and communicatively coupled to the data program loading facility and configured to selectively use one or more of the pre-loaded sound processing programs to fit the sound processor to the patient after completion of the data transfer session.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Methods and systems for fitting a sound processor to a patient are described herein. As described in more detail below, a fitting subsystem may be configured to pre-load program data representative of a plurality of sound processing programs onto the sound processor during a data transfer session. After completion of the data transfer session, the fitting subsystem may selectively use one or more of the pre-loaded sound processing programs to fit the sound processor to the patient.

As used herein, the term "sound processing program" refers to any program that is executable by a sound processor included in a cochlear implant system. Hence, a sound processing program may specify a particular mode in which the sound processor is to operate. For example, a sound processing program may define a set of control parameters selected to optimize a listening experience of a cochlear implant patient in a particular listening environment (e.g., a relatively quiet room, a noisy restaurant, a musical environment, etc.). Other sound processing programs may be configured to facilitate measurement of one or more electrode impedances, performance of one or more neural response detection operations, and/or performance of one or more diagnostics procedures associated with the cochlear implant system. As will be described in more detail below, the fitting subsystem may adjust one or more control parameters associated with a particular sound processing program in response to patient feedback and/or user input in order to customize the sound processing program to the cochlear implant patient.

Numerous advantages may be associated with the methods and systems described herein. For example, by pre-loading program data representative of a plurality of sound processing programs onto the sound processor before commencing a fitting session in which the sound processor is fitted to a patient, the fitting subsystem may rapidly switch between the sound processing programs without experiencing the relatively substantial delay that is associated with loading each sound processing program onto the sound processor each time it is to be executed by the sound processor. In this manner, a sound processor may be more effectively fitted to the patient.

Figure 1:
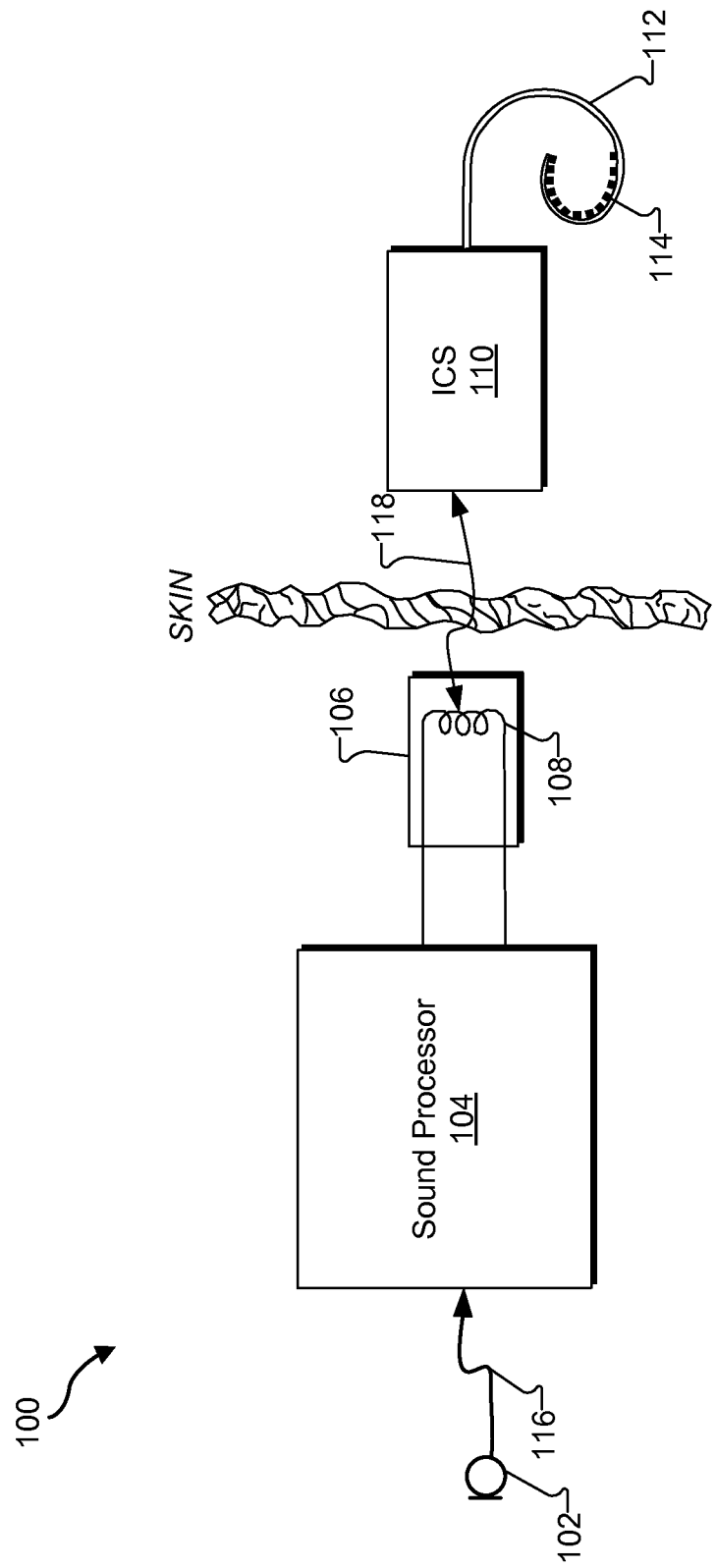
FIG. 1 illustrates an exemplary cochlear implant system according to principles described herein.

To facilitate an understanding of the methods and systems described herein, an exemplary cochlear implant system 100 will be described in connection with FIG. 1. As shown in FIG. 1, cochlear implant system 100 may include a microphone 102, a sound processor 104, a headpiece 106 having a coil 108 disposed therein, an implantable cochlear stimulator ("ICS") 110, and a lead 112 with a plurality of electrodes 114 disposed thereon. Additional or alternative components may be included within cochlear implant system 100 as may serve a particular implementation.

As shown in FIG. 1, microphone 102, sound processor 104, and headpiece 106 may be located external to a cochlear implant patient. In some alternative examples, microphone 102 and/or sound processor 104 may be implanted within the patient. In such configurations, the need for headpiece 106 may be obviated.

Microphone 102 may detect an audio signal and convert the detected signal to a corresponding electrical signal. The electrical signal may be sent from microphone 102 to sound processor 104 via a communication link 116, which may include a telemetry link, a wire, and/or any other suitable communication link.

Sound processor 104 is configured to direct implantable cochlear stimulator 110 to generate and apply electrical stimulation (also referred to herein as "stimulation current") to one or more stimulation sites within a cochlea of the patient. To this end, sound processor 104 may process the audio signal detected by microphone 102 in accordance with a selected sound processing strategy to generate appropriate stimulation parameters for controlling implantable cochlear stimulator 110. Sound processor 104 may include or be implemented by a behind-the-ear ("BTE") unit, a portable speech processor ("PSP"), and/or any other sound processing unit as may serve a particular implementation. Exemplary components of sound processor 104 will be described in more detail below.

Sound processor 104 may be configured to transcutaneously transmit one or more control parameters and/or one or more power signals to implantable cochlear stimulator 110 with coil 108 by way of a communication link 118. These control parameters may be configured to specify one or more stimulation parameters, operating parameters, and/or any other parameter by which implantable cochlear stimulator 110 is to operate as may serve a particular implementation. Exemplary control parameters include, but are not limited to, stimulation current levels, volume control parameters, program selection parameters, operational state parameters (e.g., parameters that turn a sound processor and/or an implantable cochlear stimulator on or off), audio input source selection parameters, fitting parameters, noise reduction parameters, microphone sensitivity parameters, microphone direction parameters, pitch parameters, timbre parameters, sound quality parameters, most comfortable current levels ("M levels"), threshold current levels, channel acoustic gain parameters, front and backend dynamic range parameters, current steering parameters, pulse rate values, pulse width values, frequency parameters, amplitude parameters, waveform parameters, electrode polarity parameters (i.e., anode-cathode assignment), location parameters (i.e., which electrode pair or electrode group receives the stimulation current), stimulation type parameters (i.e., monopolar, bipolar, or tripolar stimulation), burst pattern parameters (e.g., burst on time and burst off time), duty cycle parameters, spectral tilt parameters, filter parameters, and dynamic compression parameters. Sound processor 104 may also be configured to operate in accordance with one or more of the control parameters.

As shown in FIG. 1, coil 108 may be housed within headpiece 106, which may be affixed to a patient's head and positioned such that coil 108 is communicatively coupled to a corresponding coil included within implantable cochlear stimulator 110. In this manner, control parameters and power signals may be wirelessly transmitted between sound processor 104 and implantable cochlear stimulator 110 via communication link 118. It will be understood that data communication link 118 may include a bi-directional communication link and/or one or more dedicated uni-directional communication links. In some alternative embodiments, sound processor 104 and implantable cochlear stimulator 110 may be directly connected with one or more wires or the like.

Implantable cochlear stimulator 110 may be configured to generate electrical stimulation representative of an audio signal detected by microphone 102 in accordance with one or more stimulation parameters transmitted thereto by sound processor 104. Implantable cochlear stimulator 110 may be further configured to apply the electrical stimulation to one or more stimulation sites within the cochlea via one or more electrodes 114 disposed along lead 112. In some examples, implantable cochlear stimulator 110 may include a plurality of independent current sources each associated with a channel defined by one or more of electrodes 114. In this manner, different stimulation current levels may be applied to multiple stimulation sites simultaneously by way of multiple electrodes 114. In such examples, cochlear implant system 100 may be referred to as a "multi-channel cochlear implant system."

To facilitate application of the electrical stimulation generated by implantable cochlear stimulator 110, lead 112 may be inserted within a duct of the cochlea such that electrodes 114 are in communication with one or more stimulation sites within the cochlea. As used herein, the term "in communication with" refers to electrodes 114 being adjacent to, in the general vicinity of, in close proximity to, directly next to, or directly on the stimulation site. Any number of electrodes 114 (e.g., sixteen) may be disposed on lead 112 as may serve a particular implementation.

Figure 2:
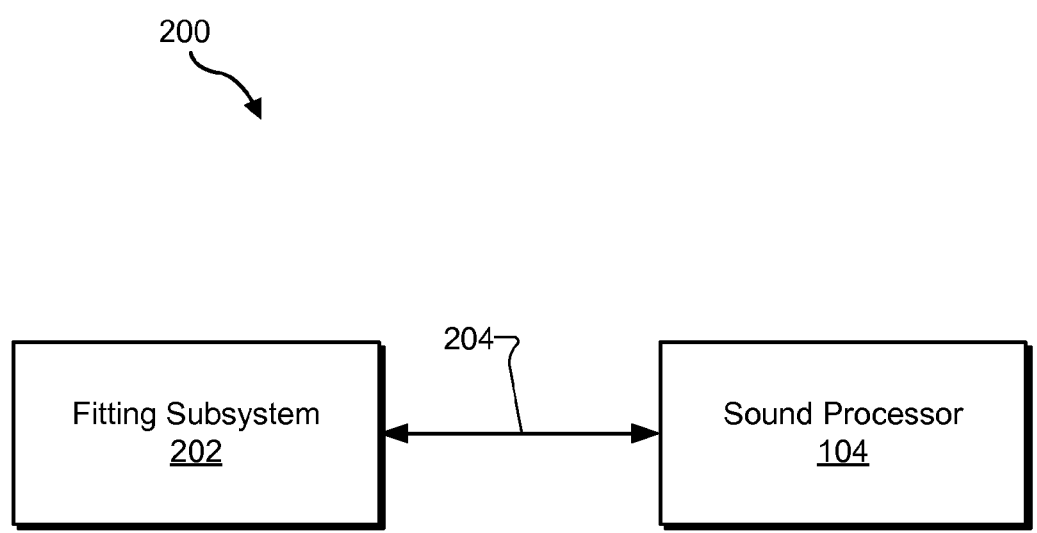
FIG. 2 illustrates an exemplary cochlear implant fitting system according to principles described herein.

FIG. 2 illustrates an exemplary cochlear implant fitting system 200 (or simply "fitting system 200") that may be used to fit sound processor 104 to a patient. As used herein, the terms "fitting a sound processor to a patient" and "fitting a cochlear implant system to a patient" will be used interchangeably to refer to performing one or more fitting operations associated with sound processor 104 and/or any other component of cochlear implant system 100. Such fitting operations may include, but are not limited to, adjusting one or more control parameters by which sound processor 104 and/or implantable cochlear stimulator 110 operate, measuring one or more electrode impedances, performing one or more neural response detection operations, and/or performing one or more diagnostics procedures associated with the cochlear implant system.

As shown in FIG. 2, fitting system 200 may include a fitting subsystem 202 configured to be selectively and communicatively coupled to sound processor 104 of cochlear implant system 100 by way of a communication link 204. Fitting subsystem 202 and sound processor 104 may communicate using any suitable communication technologies, devices, networks, media, and protocols supportive of data communications.

Fitting subsystem 202 may be configured to perform one or more of the fitting operations described herein. To this end, fitting subsystem 202 may be implemented by any suitable combination of computing and communication devices including, but not limited to, a fitting station, a personal computer, a laptop computer, a handheld device, a mobile device (e.g., a mobile phone), a clinician's programming interface ("CPI") device, and/or any other suitable component as may serve a particular implementation. An exemplary implementation of fitting subsystem 202 will be described in more detail below.

Figure 3:
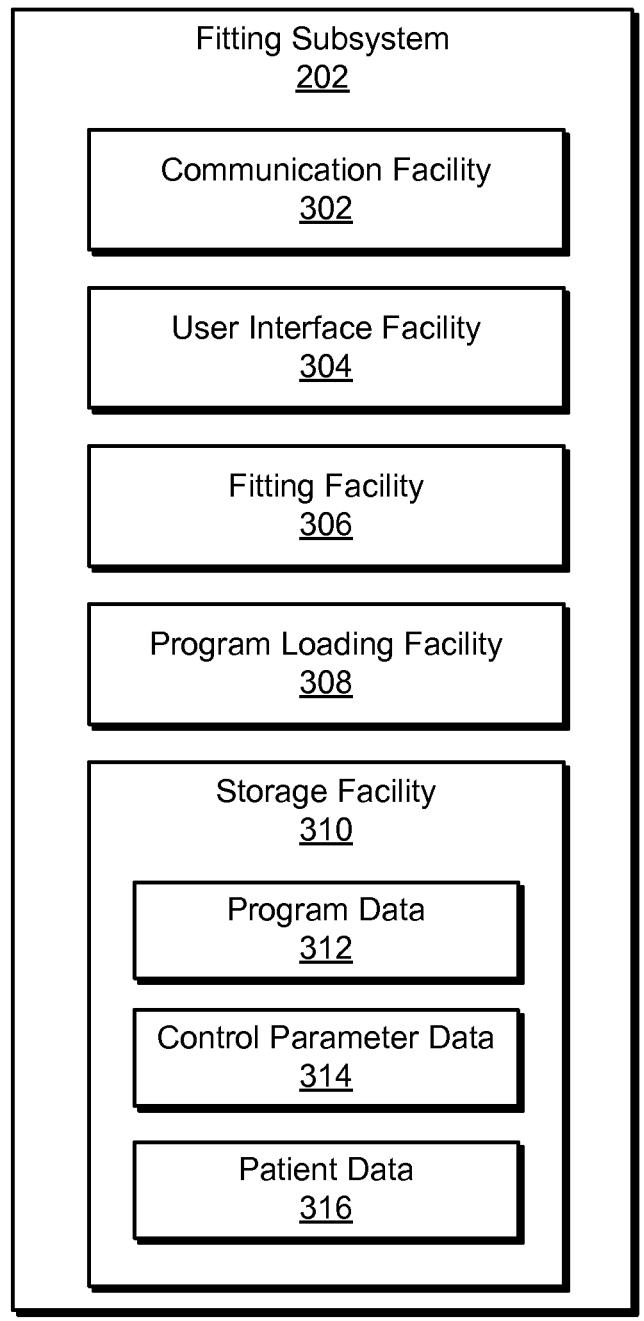
FIG. 3 illustrates exemplary components of an exemplary fitting subsystem according to principles described herein.

FIG. 3 illustrates exemplary components of fitting subsystem 202. As shown in FIG. 3, fitting subsystem 202 may include a communication facility 302, a user interface facility 304, a fitting facility 306, a program loading facility 308, and a storage facility 310, which may be communicatively coupled to one another using any suitable communication technologies. Each of these facilities will now be described in more detail.

Communication facility 302 may be configured to facilitate communication between fitting subsystem 202 and sound processor 104. For example, communication facility 302 may be implemented by a CPI device, which may include any suitable combination of components configured to allow fitting subsystem 202 to interface and communicate with sound processor 104. Communication facility 302 may additionally or alternatively include one or more transceiver components configured to wirelessly transmit data (e.g., program data and/or control parameter data) to sound processor 104 and/or wirelessly receive data (e.g., feedback data, impedance measurement data, neural response data, etc.) from sound processor 104.

Communication facility 302 may additionally or alternatively be configured to facilitate communication between fitting subsystem 302 and one or more other devices. For example, communication facility 302 may be configured to facilitate communication between fitting subsystem 302 and one or more computing devices (e.g., by way of the Internet and/or one or more other types of networks), reference implants, and/or any other computing device as may serve a particular implementation.

User interface facility 304 may be configured to provide one or more user interfaces configured to facilitate user interaction with fitting subsystem 202. For example, user interface facility 304 may provide a graphical user interface ("GUI") through which one or more functions, options, features, and/or tools associated with one or more fitting operations described herein may be provided to a user and through which user input may be received. In certain embodiments, user interface facility 304 may be configured to provide the GUI to a display device (e.g., a computer monitor) for display.

Fitting facility 306 may be configured to perform one or more of the fitting operations described herein. For example, fitting facility 306 may be configured to adjust one or more control parameters by which sound processor 104 and/or implantable cochlear stimulator 110 operate, direct sound processor 104 to measure one or more electrode impedances, perform one or more neural response detection operations, and/or perform one or more diagnostics procedures associated with cochlear implant system 100.

In some examples, fitting facility 306 may be configured to selectively use one or more sound processing programs that have been pre-loaded onto sound processor 104 to fit sound processor 104 to a patient. The pre-loading of the one or more sound processing programs may be performed by program loading facility 308, as will be described in more detail below. Exemplary manners in which fitting facility may selectively use one or more sound processing programs that have been pre-loaded onto sound processor 104 to fit sound processor 104 to a patient will be described in more detail below.

In some examples, fitting facility 306 may be configured to initialize sound processor 104 prior to fitting sound processor 104 to a patient. Such initialization may include, but is not limited to, associating sound processor 104 with a particular patient (e.g., associating sound processor 104 with patient-specific fitting data), associating sound processor 104 with a particular implantable cochlear stimulator 110, loading data onto sound processor 104, clearing data from sound processor 104, and/or otherwise preparing sound processor 104 for a fitting session in which sound processor 104 is to be fitted to a patient.

Program loading facility 308 may be configured to load data representative of one or more sound processing programs onto sound processor 104 for use by sound processor 104 during and/or after a fitting session. In some examples, program loading facility 308 may be configured to pre-load program data representative of a plurality of sound processing programs onto sound processor 104 during a data transfer session. In this manner, as will be described in more detail below, a user (e.g., an audiologist) of fitting subsystem 202 may direct sound processor 104 to switch between multiple sound processing programs during a fitting session in substantially real-time without having to wait for each sound processing program to be individually loaded onto sound processor 104 each time it is to be executed by sound processor 104.

In some examples, program loading facility 308 may be configured to pre-load program data representative of a plurality of sound processing programs onto sound processor 104 by transmitting the program data to sound processor 104 and directing sound processor to cache the program data as a library of sound processing programs in a storage medium (e.g., memory) included within sound processor 104. The program data may include any type of data (e.g., digital signal processing ("DSP") code) and may be cached within sound processor 104 for any amount of time as may serve a particular implementation.

Additionally or alternatively, program loading facility 308 may associate one or more pre-loaded sound processing programs with one or more slots associated with sound processor 104 using any suitable "write-to-slot" operation. As used herein, a "slot" is a logical concept associating a sound processing program and a set of control parameters with one of a plurality of program positions selectable via a hardware switch disposed on a sound processor (e.g., sound processor 104). When a specific slot is selected, the sound processor locates the sound processing program for that slot, begins executing the located sound processing program, and points the executed sound processing program at the set of control parameters that are also associated with that slot. Because the sound processing programs are already pre-loaded onto sound processor 104, the speed at which a write-to-slot operation occurs may be relatively fast.

In some examples, program loading facility 308 may be implemented by one or more computing devices located at a site associated with a manufacturer of sound processor 104 (e.g., a factory of the manufacturer and/or a factory of a third-party entity contracted or otherwise associated with the manufacturer). In this manner, the pre-loading of the program data may be performed by the manufacturer before sound processor 104 is delivered to the patient.

Additionally or alternatively, program loading facility 308 may be implemented by a fitting station and/or other computing device utilized by a clinician to fit sound processor 104 to a patient. In this manner, the pre-loading of the program data may be performed during an initialization of sound processor 104 and/or at any point during or after a fitting session in which sound processor 104 is fit to the patient.

Storage facility 310 may be configured to maintain program data 312 representative of one or more sound processing programs, control parameter data 314 representative of one or more control parameters, and patient data 316 representative of data descriptive of or otherwise associated with one or more cochlear implant patients. Storage facility 310 may be configured to maintain additional or alternative data as may serve a particular implementation.

Figure 4:
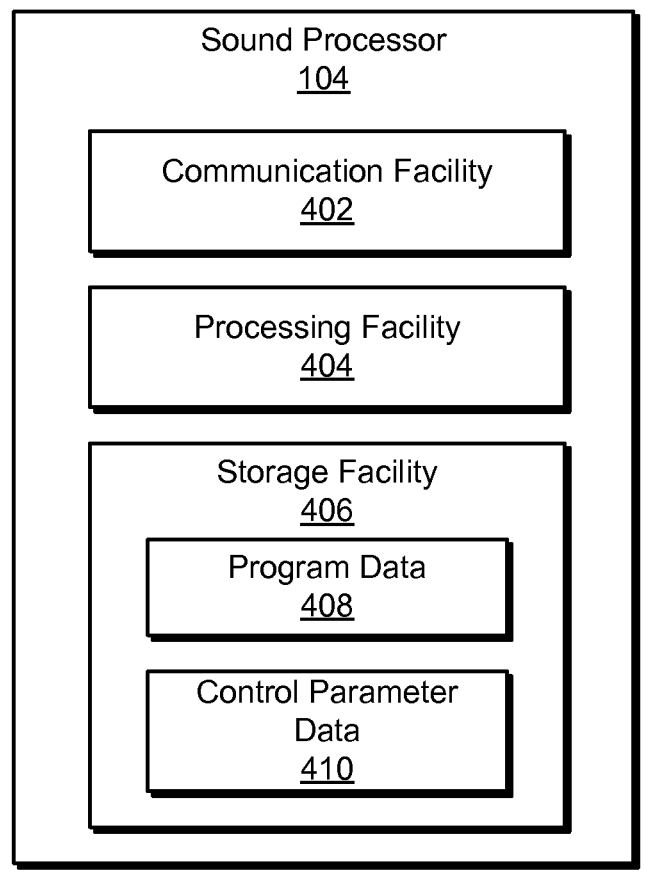
FIG. 4 illustrates exemplary components of a sound processor according to principles described herein.

FIG. 4 illustrates exemplary components of sound processor 104. As shown in FIG. 4, sound processor 104 may include a communication facility 402, a processing facility 404, and a storage facility 406, any or all of which may be in communication with one another using any suitable communication technologies. Each of these facilities will now be described in more detail.

Communication facility 402 may be configured to facilitate communication between sound processor 104 and fitting subsystem 202. For example, communication facility 402 may be configured to facilitate electrical coupling of sound processor 104 to a CPI device in order to communicate with fitting subsystem 202. Communication facility 402 may be further configured to facilitate communication between sound processor 104 and implantable cochlear stimulator 110. For example, communication facility 402 may include transceiver components configured to wirelessly transmit data (e.g., control parameters and/or power signals) to implantable cochlear stimulator 110 and/or wirelessly receive data from implantable cochlear stimulator 110.

Processing facility 404 may be configured to perform one or more signal processing heuristics on an audio signal presented to the patient. For example, processing facility 404 may perform one or more pre-processing operations, spectral analysis operations, noise reduction operations, mapping operations, and/or any other types of signal processing operations on a detected audio signal as may serve a particular implementation. In some examples, processing facility 404 may generate and/or adjust one or more control parameters governing an operation of implantable cochlear stimulator 110 (e.g., one or more stimulation parameters defining the electrical stimulation to be generated and applied by implantable cochlear stimulator 110). In some examples, processing facility 404 may be configured to operate (e.g., process incoming audio signals and/or control implantable cochlear stimulator 110) in accordance with one or more sound processing programs provided by fitting subsystem 202 and/or otherwise stored within storage facility 406.

Storage facility 406 may be configured to maintain program data 408 representative of one or more sound processing programs (which, as described above, may be pre-loaded onto sound processor 104) and control parameter data 410 representative of one or more control parameters. Storage facility 406 may be configured to maintain additional or alternative data as may serve a particular implementation.

Figure 5:
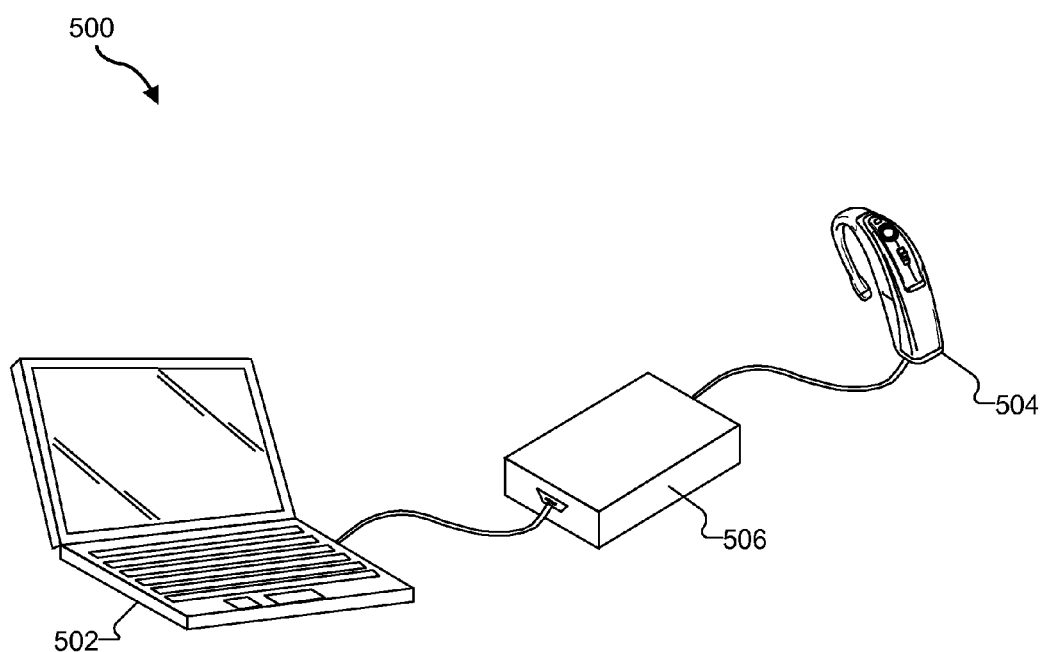
FIG. 5 illustrates an exemplary implementation of the cochlear implant fitting system of FIG. 2 according to principles described herein.

FIG. 5 illustrates an exemplary implementation 500 of fitting system 200. In implementation 500, a fitting station 502 may be selectively and communicatively coupled to a BTE unit 504 by way of a CPI device 506. BTE unit 504 is merely exemplary of the many different types of sound processors that may be used in accordance with the systems and methods described herein. Fitting station 502 may be selectively and communicatively coupled to any other type of sound processor as may serve a particular implementation.

Fitting station 502 may include any suitable computing device and/or combination of computing devices and be configured to perform one or more of the fitting operations described herein. For example, fitting station 502 may display one or more GUIs configured to facilitate pre-loading of one or more sound processing programs onto BTE unit 504, selection of one or more sound processing programs by which BTE unit 504 operates, adjustment of one or more control parameters by which BTE unit 504 operates, and/or any other fitting operation as may serve a particular implementation. Fitting station 502 may be utilized by an audiologist, a clinician, and/or any other user to fit BTE unit 504 to a patient.

In some examples, fitting station 502 may be located at a site associated with a manufacturer of BTE unit 504 (e.g., a factory of the manufacturer and/or a factory of a third-party entity contracted or otherwise associated with the manufacturer). In this manner, fitting station 502 may be used to pre-load program data onto BTE unit 504 before BTE unit 504 is delivered to the patient.

CPI device 506 may be configured to facilitate communication between fitting station 502 and BTE unit 504. In some examples, CPI device 506 may be selectively and communicatively coupled to fitting station 502 and/or BTE unit 504 by way of one or more ports included within fitting station 502 and BTE unit 504.

Figure 6:
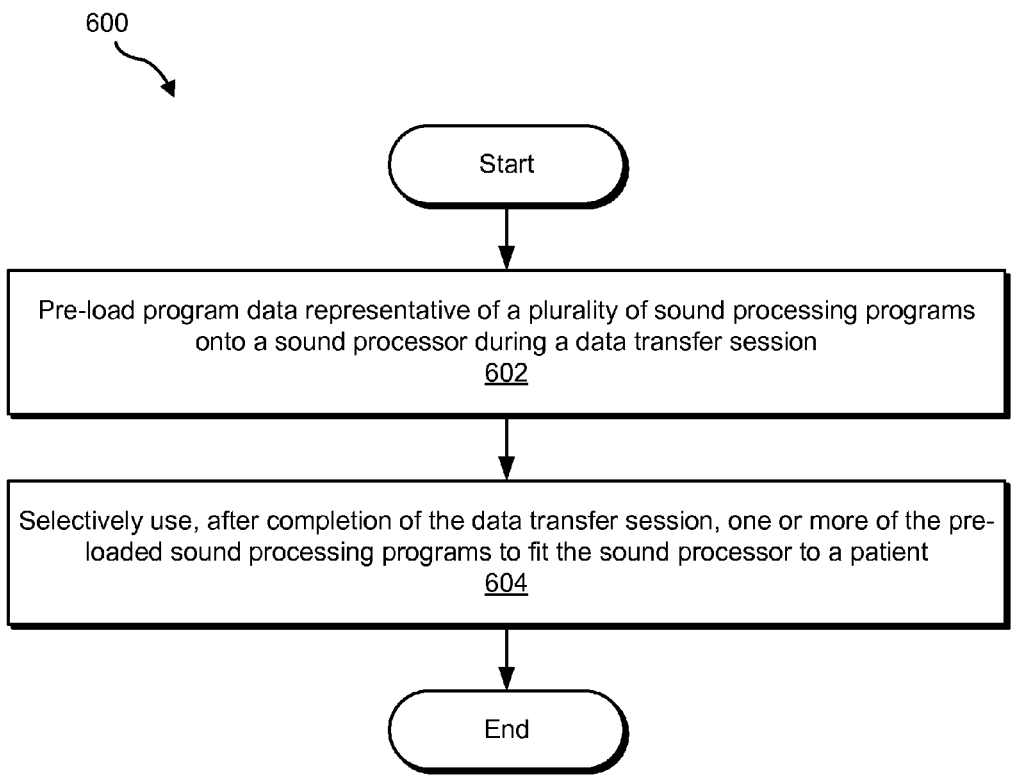
FIG. 6 illustrates an exemplary method of fitting a sound processor to a patient according to principles described herein.

FIG. 6 illustrates an exemplary method 600 of fitting a sound processor to a patient. While FIG. 6 illustrates exemplary steps according to one embodiment, other embodiments may omit, add to, reorder, and/or modify any of the steps shown in FIG. 6. One or more of the steps shown in FIG. 6 may be performed by any component or combination of components of fitting subsystem 202 and/or fitting station 502.

In step 602, program data representative of a plurality of sound processing programs is pre-loaded onto a sound processor (e.g., sound processor 104) during a data transfer session. As described above, the program data may be pre-loaded onto the sound processor by a manufacturer of the sound processor prior to the sound processor being delivered to a patient, during an initialization of the sound processor, and/or at any point before or during a fitting session in which the sound processor is fitted to a patient.

In some examples, step 602 may be performed by transmitting the program data to the sound processor and directing the sound processor to cache the program data as a library of sound processing programs in a storage medium included within the sound processor.

In step 604, after completion of the data transfer session, one or more of the pre-loaded sound processing programs are selectively used to fit the sound processor to a cochlear implant patient. Because the program data has been pre-loaded onto the sound processor, a user of fitting subsystem 202 may rapidly switch between the sound processing programs during a fitting session without experiencing the relatively substantial delay that is associated with loading each sound processing program onto the sound processor each time it is to be executed by the sound processor.

Figure 7A:
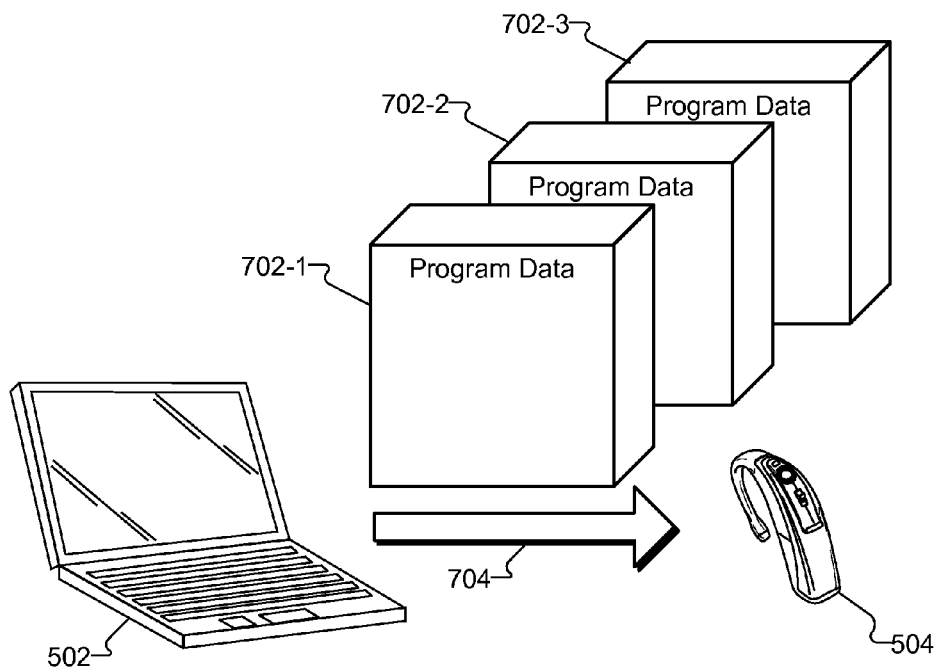
FIGS. 7A-7B illustrate an exemplary time-saving benefit of pre-loading program data representative of multiple sound processing programs onto a sound processor according to principles described herein.
Figure 7B:
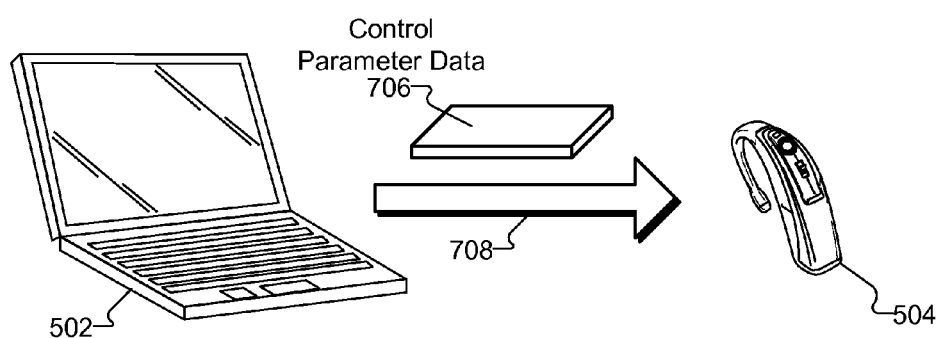

FIGS. 7A-7B illustrate an exemplary time-saving benefit of pre-loading program data representative of multiple sound processing programs onto a sound processor during a data transfer session that occurs before a fitting session in which one or more of the sound processing programs are used to fit the sound processor to a patient. As shown in FIG. 7A, program data 702 (e.g., program data 702-1, 702-2, and 702-3) representative of three different sound processing programs may be pre-loaded onto BTE unit 504 by fitting station 502 during a data transfer session. The pre-loading is represented in FIG. 7A by arrow 704.

As illustrated in FIG. 7A, program data 702 corresponding to each sound processing program may be relatively large in size. Because the data transfer speed may be relatively slow between fitting station 502 and BTE unit 504, it may take a relatively long time to load program data 702 onto BTE unit 504. Hence, if program data (e.g., program data 702-1) associated with an individual sound processing program has to be loaded onto BTE unit 504 each time an audiologist or other user directs BTE unit 504 to operate in accordance with the sound processing program, substantial delays may be incurred, which may interrupt or otherwise interfere with a fitting session in which BTE unit 504 is fitted to a patient.

Hence, all of the program data 702-1, 702-2, and 702-3 may be pre-loaded onto BTE unit 504 during a single data transfer session that precedes the fitting session. In this manner, BTE unit 504 may switch between and/or execute one or more of the sound processing programs represented by program data 702-1, 702-2, and 702-3 in substantially real-time.

FIG. 7B illustrates that control parameter data 706 representative of one or more control parameters associated with a sound processing program selected for execution by BTE unit 504 may be transmitted by fitting station 502 to BTE unit 504 during a fitting session. Such transmission of control parameter data 706 is represented by arrow 708. The one or more control parameters may define which of the sound processing programs pre-loaded onto BTE unit 504 is to be executed and/or how the selected sound processing program is executed.

As graphically illustrated in FIGS. 7A and 7B, control parameter data 706 is typically substantially smaller in size than program data 702. Hence, control parameter data 706 may be transmitted to BTE unit 504 in a relatively short amount of time compared to the time it takes program data (e.g., program data 702-1) representative of a sound processing program to be transmitted to BTE unit 504.

Returning to FIG. 6, step 604 may be performed by providing a GUI configured to facilitate interaction by a user with the plurality of sound processing programs, receiving user input representative of a selection of a sound processing program included in the plurality of sound processing programs by way of the GUI, and directing, in response to the user input, the sound processor to operate in accordance with the selected sound processing program. If the user desires to switch to another sound processing program, the user may provide additional user input representative of a selection of the other sound processing program by way of the GUI. In response to the additional user input, fitting subsystem 202 may direct the sound processor to dynamically cease operating in accordance with the initially selected sound processing program and begin operating in accordance with the newly selected sound processing program.

Figure 8:
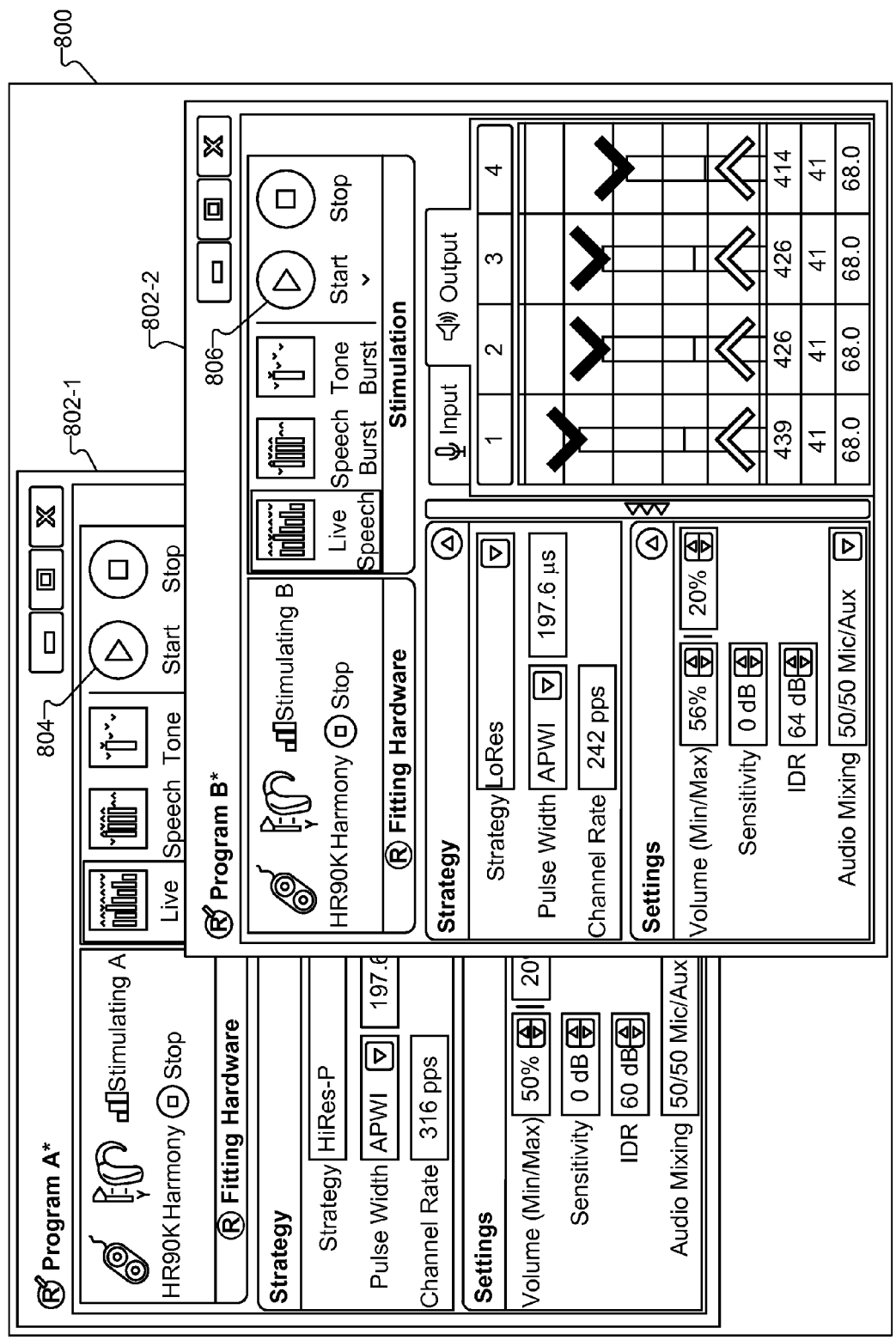
FIG. 8 shows an exemplary graphical user interface ("GUI") that may be presented for display according to principles described herein.

To illustrate, FIG. 8 shows an exemplary GUI 800 that may be presented for display by fitting subsystem 202. It will be recognized that GUI 800 is merely illustrative of the many different GUIs that may be presented for display by fitting subsystem 202. As shown in FIG. 8, GUI 800 may include a plurality of distinct windows 802 (e.g., windows 802-1 and 802-2) each corresponding to a particular sound processing program that has been pre-loaded onto sound processor 104. In the example of FIG. 8, window 802-1 corresponds to a sound processing program named "program A" and window 802-2 corresponds to a sound processing program named "program B".

A user of fitting subsystem 202 may switch between windows 802 to access information associated with programs A and B, adjust one or more control parameters associated with each of programs A and B, and/or selectively start, stop, and/or resume an execution of programs A and B. For example, a user of fitting subsystem 202 may select window 802-1, provide user input representative of one or more control parameters values to be used by sound processor 104 while operating in accordance with program A, and select a "start option" 804 to direct sound processor 104 to begin operating in accordance with program A. While program A is being executed by sound processor 104 or at any time thereafter, the user may select window 802-2, provide user input representative of one or more control parameters values to be used by sound processor 104 while operating in accordance with program B, and select a "start option" 806 to direct sound processor 104 to dynamically cease operating in accordance with program A and to begin operating in accordance with program B. In this manner, the user may dynamically and rapidly switch between programs A and B in order to more effectively fit sound processor 104 to a patient.

Figure 9:
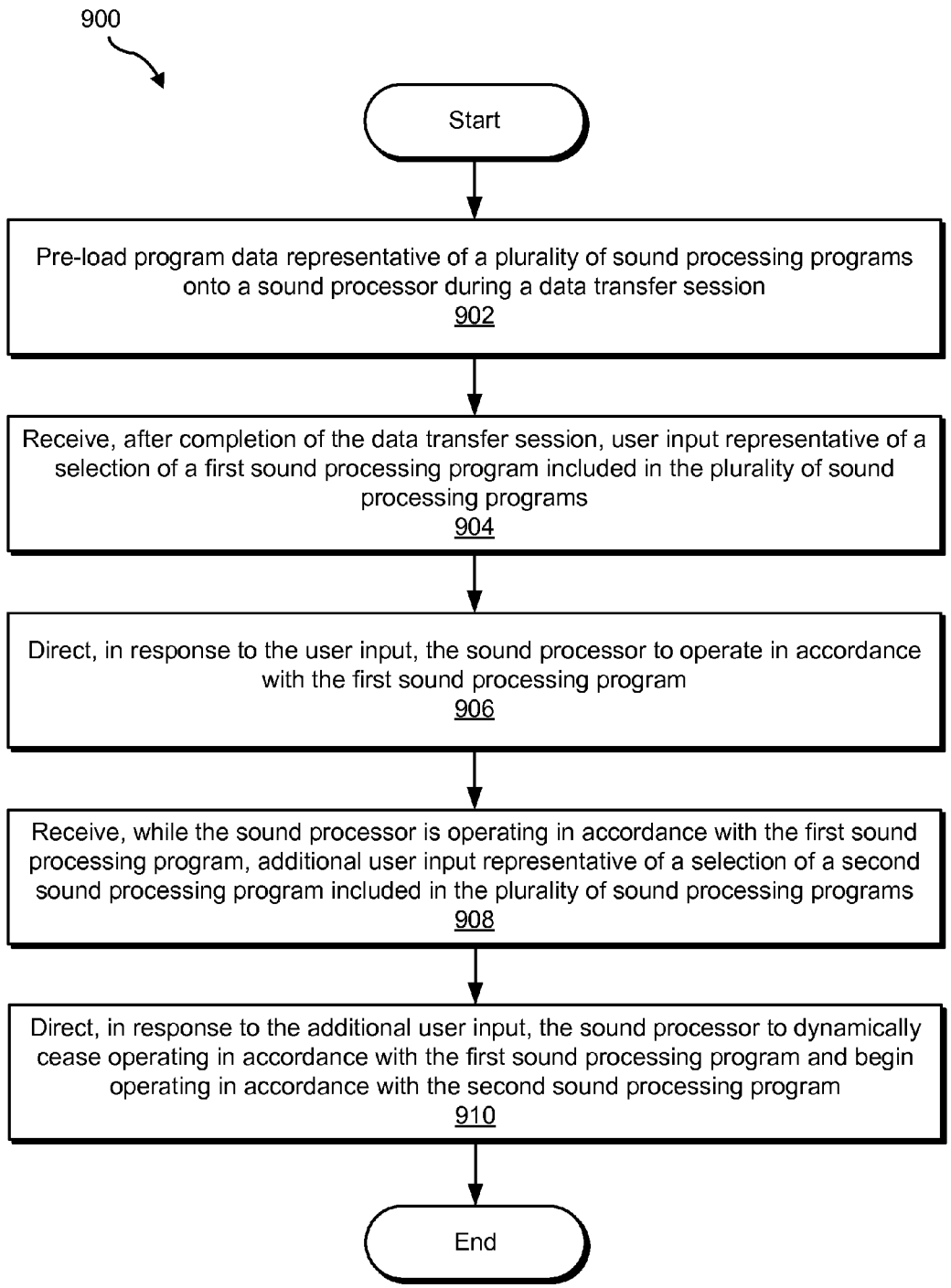
FIG. 9 illustrates another exemplary method of fitting a sound processor to a patient according to principles described herein.

FIG. 9 illustrates another exemplary method 900 of fitting a sound processor to a patient. While FIG. 9 illustrates exemplary steps according to one embodiment, other embodiments may omit, add to, reorder, and/or modify any of the steps shown in FIG. 9. One or more of the steps shown in FIG. 9 may be performed by any component or combination of components of fitting subsystem 202 and/or fitting station 502.

In step 902, program data representative of a plurality of sound processing programs is pre-loaded onto a sound processor during a data transfer session. Step 902 may be performed in any of the ways described herein.

In step 904, after completion of the data transfer session, user input representative of a selection of a first sound processing program included in the plurality of sound processing programs is received. Step 904 may be performed in any of the ways described herein.

In step 906, the sound processor is directed to operate in accordance with the first sound processing program in response to the user input. Step 906 may be performed in any of the ways described herein.

In step 908, additional user input representative of a selection of a second sound processing program included in the plurality of sound processing programs is received while the sound processor is operating in accordance with the first sound processing program. Step 908 may be performed in any of the ways described herein.

In step 910, the sound processor is directed, in response to the additional user input, to dynamically cease operating in accordance with the first sound processing program and begin operating in accordance with the second sound processing program. Step 910 may be performed in any of the ways described herein.

In certain embodiments, one or more of the components and/or processes described herein may be implemented and/or performed by one or more appropriately configured computing devices. To this end, one or more of the systems and/or components described above may include or be implemented by any computer hardware and/or computer-implemented instructions (e.g., software) embodied on a non-transitory computer-readable medium configured to perform one or more of the processes described herein. In particular, system components may be implemented on one physical computing device or may be implemented on more than one physical computing device. Accordingly, system components may include any number of computing devices, and may employ any of a number of computer operating systems.

In certain embodiments, one or more of the processes described herein may be implemented at least in part as instructions executable by one or more computing devices. In general, a processor (e.g., a microprocessor) receives instructions, from a tangible computer-readable medium, (e.g., a memory, etc.), and executes those instructions, thereby performing one or more processes, including one or more of the processes described herein. Such instructions may be stored and/or transmitted using any of a variety of known non-transitory computer-readable media.

A non-transitory computer-readable medium (also referred to as a processor-readable medium) includes any non-transitory medium that participates in providing data (e.g., instructions) that may be read by a computer (e.g., by a processor of a computer). Such a non-transitory medium may take many forms, including, but not limited to, non-volatile media and/or volatile media. Non-volatile media may include, for example, optical or magnetic disks and other persistent memory. Volatile media may include, for example, dynamic random access memory ("DRAM"), which typically constitutes a main memory. Common forms of non-transitory computer-readable media include, for example, a floppy disk, flexible disk, hard disk, magnetic tape, any other magnetic medium, a CD-ROM, DVD, any other optical medium, a RAM, a PROM, an EPROM, a FLASH-EEPROM, any other memory chip or cartridge, or any other non-transitory medium from which a computer can read.

Figure 10:
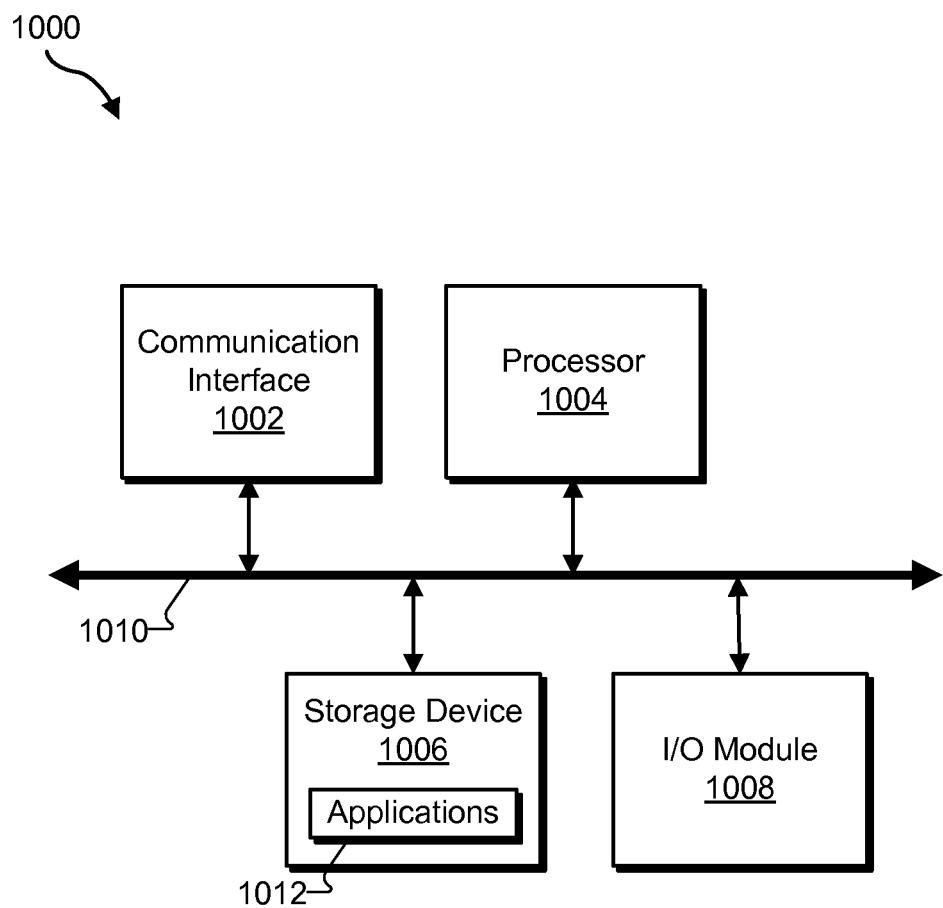
FIG. 10 illustrates an exemplary computing device according to principles described herein.

FIG. 10 illustrates an exemplary computing device 1000 that may be configured to perform one or more of the processes described herein. As shown in FIG. 10, computing device 1000 may include a communication interface 1002, a processor 1004, a storage device 1006, and an input/output ("I/O") module 1008 communicatively connected via a communication infrastructure 1010. While an exemplary computing device 1000 is shown in FIG. 10, the components illustrated in FIG. 10 are not intended to be limiting. Additional or alternative components may be used in other embodiments. Components of computing device 1000 shown in FIG. 10 will now be described in additional detail.

Communication interface 1002 may be configured to communicate with one or more computing devices. Examples of communication interface 1002 include, without limitation, a wired network interface (such as a network interface card), a wireless network interface (such as a wireless network interface card), a modem, and any other suitable interface. Communication interface 1002 may additionally or alternatively provide such a connection through, for example, a local area network (such as an Ethernet network), a personal area network, a telephone or cable network, a satellite data connection, a dedicated URL, or any other suitable connection. Communication interface 1002 may be configured to interface with any suitable communication media, protocols, and formats, including any of those mentioned above.

Processor 1004 generally represents any type or form of processing unit capable of processing data or interpreting, executing, and/or directing execution of one or more of the instructions, processes, and/or operations described herein. Processor 1004 may direct execution of operations in accordance with one or more applications 1012 or other computer-executable instructions such as may be stored in storage device 1006 or another non-transitory computer-readable medium.

Storage device 1006 may include one or more data storage media, devices, or configurations and may employ any type, form, and combination of data storage media and/or device. For example, storage device 1006 may include, but is not limited to, a hard drive, network drive, flash drive, magnetic disc, optical disc, random access memory ("RAM"), dynamic RAM ("DRAM"), other non-volatile and/or volatile data storage units, or a combination or sub-combination thereof. Electronic data, including data described herein, may be temporarily and/or permanently stored in storage device 1006. For example, data representative of one or more executable applications 1012 (which may include, but are not limited to, one or more of the software applications described herein) configured to direct processor 1004 to perform any of the operations described herein may be stored within storage device 1006. In some examples, data may be arranged in one or more databases residing within storage device 1006.

I/O module 1008 may be configured to receive user input and provide user output and may include any hardware, firmware, software, or combination thereof supportive of input and output capabilities. For example, I/O module 1008 may include hardware and/or software for capturing user input, including, but not limited to, a keyboard or keypad, a touch screen component (e.g., touch screen display), a receiver (e.g., an RF or infrared receiver), and/or one or more input buttons.

I/O module 1008 may include one or more devices for presenting output to a user, including, but not limited to, a graphics engine, a display (e.g., a display screen, one or more output drivers (e.g., display drivers), one or more audio speakers, and one or more audio drivers. In certain embodiments, I/O module 1008 is configured to provide graphical data to a display for presentation to a user. The graphical data may be representative of one or more graphical user interfaces and/or any other graphical content as may serve a particular implementation.

In some examples, any of the facilities described herein may be implemented by or within one or more components of computing device 1000. For example, one or more applications 1012 residing within storage device 1006 may be configured to direct processor 1004 to perform one or more processes or functions associated with communication facility 302, user interface facility 304, fitting facility 306, program loading facility 308, communication facility 402, and/or processing facility 404. Likewise, storage facility 310 and/or storage facility 406 may be implemented by or within storage device 1006.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A method comprising:
pre-loading, by a fitting subsystem that is separate from a sound processor, a plurality of independently executable sound processing programs onto a sound processor during a data transfer session while the sound processor is selectively and communicatively coupled to the fitting subsystem, wherein each independently executable sound processing program included in said plurality of independently executable sound processing programs is associated with a distinct set of control parameters; and
selectively using, by the fitting subsystem after completion of the data transfer session and while the sound processor is still selectively and communicatively coupled to the fitting subsystem, the pre-loaded independently executable sound processing programs to fit the sound processor to a cochlear implant patient by directing the sound processor to switch between executing the pre-loaded independently executable sound processing programs during a fitting session in response to user input by
presenting a graphical user interface by way of a display screen that is a part of the fitting subsystem, the graphical user interface including
a first window corresponding to a first independently executable sound processing program included in the plurality of independently executable sound processing programs, and
a second window corresponding to a second independently executable sound processing program included in the plurality of independently executable sound processing programs,
receiving, by way of the graphical user interface, first user input representative of a selection of a first option displayed in the first window, and
directing, in response to the first user input, the sound processor to operate in accordance with the first independently executable sound processing program.

2. The method of claim 1, wherein the pre-loading comprises:
transmitting the plurality of independently executable sound processing programs to the sound processor; and
directing the sound processor to cache the plurality of independently executable sound processing programs in a storage medium included within the sound processor.

3. The method of claim 1, wherein the pre-loading is performed prior to the sound processor being delivered to the patient.

4. The method of claim 1, further comprising initializing, by the fitting system, the sound processor, wherein the pre-loading is performed during the initializing.

5. The method of claim 1, wherein the directing the sound processor to switch between executing the pre-loaded independently executable sound processing programs during the fitting session further comprises:
receiving, by way of the graphical user interface while the sound processor is operating in accordance with the first independently executable sound processing program, second user input representative of a selection of a second option displayed in the second window; and
directing, in response to the second user input, the sound processor to dynamically cease operating in accordance with the first independently executable sound processing program and begin operating in accordance with the second independently executable sound processing program.

6. The method of claim 1, further comprising facilitating adjustment of one or more control parameters in the distinct set of control parameters associated with one or more of the independently executable sound processing programs by way of the graphical user interface.

7. The method of claim 1, wherein the selectively using of the one or more of the pre-loaded independently executable sound processing programs to fit the sound processor to the patient further comprises:
receiving additional user input representative of a request to adjust one or more control parameters in the distinct set of control parameters associated with a particular independently executable sound processing program included in the plurality of independently executable sound processing programs; and
transmitting control parameter data to the sound processor in response to the user input, the control parameter data configured to direct the sound processor to adjust the one or more control parameters in accordance with the additional user input.

8. The method of claim 1, wherein the plurality of sound processing programs comprises at least one of a sound processing program configured for use in a relatively quiet environment, a sound processing program configured for use in a relatively noisy environment, a sound processing program configured for use in a musical environment, and a sound processing program configured for diagnostic use.

9. The method of claim 1, embodied as computer-executable instructions on at least one non-transitory computer-readable medium.

* * * * *